(12) United States Patent
Brown et al.

(10) Patent No.: US 8,349,295 B2
(45) Date of Patent: Jan. 8, 2013

(54) SURFACE MODIFIED AEROSOL PARTICLES, A METHOD AND APPARATUS FOR PRODUCTION THEREOF AND POWDERS AND DISPERSIONS CONTAINING SAID PARTICLES

(75) Inventors: David P. Brown, Espoo (FI); Esko I. Kauppinen, Helsinki (FI); Anna Lahde, Kirkkonummi (FI); Janne Raula, Helsinki (FI)

(73) Assignee: Teicos Pharma Oy, Helsinki (FI)

( * ) Notice: Subject to any disclaimer, the term of this patent is extended or adjusted under 35 U.S.C. 154(b) by 320 days.

(21) Appl. No.: 12/602,228

(22) PCT Filed: May 31, 2007

(86) PCT No.: PCT/FI2007/000151
§ 371 (c)(1),
(2), (4) Date: Nov. 30, 2009

(87) PCT Pub. No.: WO2007/125159
PCT Pub. Date: Nov. 8, 2007

(65) Prior Publication Data
US 2010/0239507 A1 Sep. 23, 2010

(30) Foreign Application Priority Data
May 3, 2006 (FI) ...................... 20060428

(51) Int. Cl.
*A61K 9/14* (2006.01)
*A61K 9/72* (2006.01)
*A61K 31/045* (2006.01)
*A61K 31/56* (2006.01)

(52) U.S. Cl. .......... 424/40; 424/489; 514/169; 514/177; 514/178; 514/179; 514/180; 514/728; 514/730

(58) Field of Classification Search .................... 424/40, 424/489; 514/169, 177–180, 728, 730
See application file for complete search history.

(56) References Cited

U.S. PATENT DOCUMENTS 5,288,504 A 2/1994 Versic
6,051,257 A 4/2000 Kodas et al.
2001/0050055 A1 12/2001 Horiuchi et al.
2004/0170575 A1 9/2004 Belli et al.
2008/0254127 A1* 10/2008 Watanabe et al. ............. 424/489

FOREIGN PATENT DOCUMENTS

| CN | 1529579 | | 9/2004 |
| WO | WO 00/27363 | * | 5/2000 |
| WO | WO 01/31312 A2 | | 5/2001 |

OTHER PUBLICATIONS

"Osmium tetroxide" accessed at en.wikipedia.org/wiki/Osmium_tetroxide on Dec. 22, 2011.*
Lähde et al. "Simultaneous synthesis and coating of salbutamol sulphate nanoparticles with L-leucine in the gas phase," International Journal of Pharmaceutics 2008, 358, pp. 256-262.*
Raula et al. "Study of the dispersion behavior of L-leucine containing microparticles synthesized with an aerosol flow reactor method," Powder Technology 2007, 177, pp. 125-132.*
Photochemical definition accessed on May 2, 2012 at www.thefreedictionary.com/p/photochemical.*
Nitroglycerin, The Merck Index, 10th edition, Merck & Co., Inc.: Rahway, N.J.: 1983, entry 6453 on pp. 948.*
Felix Carroll, Perspectives on Structure and Mechanism in Organic Chemistry, Brooks/Cole Publishing Company: New York, 1998, pp. 795-804, 816-817, and 820.*
Byeon, C.C. et al. "Excited state lifetime and intersystem crossing rate of asymmetric pentaazadentate porphrin-like metal complexes," Applied Physics Letters, 2004, 84, pp. 5174-5176.*
Paul A. Sander, Handbook of Aerosol Technology, 2nd edition, Van Nostrand Reinhold Co.: New York, 1970, pp. 30.*
International Search Report, dated Oct. 8, 2007, from corresponding PCT application.

* cited by examiner

*Primary Examiner* — James H. Alstrum-Acevedo
(74) *Attorney, Agent, or Firm* — Young & Thompson

(57) ABSTRACT

A method and apparatus for multicomponent surface modified aerosol particle production suitable for, for instance, therapeutic, cosmetic or diagnostic use in which an aerosol containing an active agent is introduced in an aerosol reactor together with a surface agent or surface agent source and/or precursor and wherein the surface agent and/or surface agent precursor is volatilizable. The surface agent vapor saturation ratio is elevated so to cause it to nucleate from the gas phase. Reactor conditions are maintaining such that the active agent remains in the condensed phase and provides a surface for the surface agent to deposit on the active agent containing aerosol particle thus producing surface modified aerosol particles. The method can be used for batch or continuous production. Particles made according to the method and powders and dispersions containing the particles are also described.

14 Claims, 14 Drawing Sheets

T=170C bare fludro after 4 weeks

T=170C coated fludro after 4 weeks

T=170 °C fludro after 45 weeks

T=170 °C coated fludro after 45 weeks

SURFACE MODIFIED AEROSOL PARTICLES, A METHOD AND APPARATUS FOR PRODUCTION THEREOF AND POWDERS AND DISPERSIONS CONTAINING SAID PARTICLES

1. BACKGROUND OF THE INVENTION

1. Field of the Invention

The present invention relates to a method and apparatus for the production of surface modified aerosol particles suitable for, for instance, therapeutic, cosmetic or diagnostic use. The method can be used for batch or continuous production. The invention also includes particles made according to the invention and powders and dispersions containing said particles.

2. Description of Related Art

Surface modification of particles is important in a number of fields related to, for instance, drug delivery and medical diagnostics and the synthesis of various multicomponent materials. The production of particles with well-defined chemical and physical properties (e.g. drug particle size, structure, crystallinity) is of interest in pharmaceutical applications, since the physical properties of the particles affect the dissolution and absorption rate, and bioavailability of the drug. Control of particle surface properties for stability and storage and for varying the dissolution rate in the body for, for instance, sustained release is also desirable. Moreover, in the field of drug delivery and medical diagnostics, due to the increasing use of pulmonary delivery of medicaments and diagnostic agents, dry powders having high flowability and dispersability are needed for repeatable dosing and efficient delivery to the lung. Inhalation has become the primary route of administration in the treatment of, for instance, asthma and COPD and is becoming ever more important for systemic delivery for diseases such as diabetes. This is because, besides providing direct access to the lungs, medication delivered through the respiratory tract provides rapid and predictable onset of action and requires lower dosages compared to the oral route.

The coating of nano and microparticles with hard crystalline material can be used improve the stability of the particles. Besides improved stability the coating is often used to modify the particle size and material surface properties. The surface properties (e.g. morphology, surface charge) of the particles affect the adhesion and detachment forces, which are important factors especially for inhalation applications. Adhesion forces (e.g. Van der Waals, capillary and electrical forces) significantly influence powder flowability (and thus dose repeatability) and aerosolisation of the powders and drug and carrier particle deagglomeration during delivery. In addition, coating can enable the controlled release of the active pharmaceutical agents that provides a way to avoid drug toxicity while delivering an optimum dose.

Numerous methods have been proposed to control the size, composition, morphology and crystalline structure and composition of inhalation powders using, for instance, precipitation or crystallization followed by drying and milling, supercritical fluid methods and spray drying. Conventional methods for the coating of pharmaceutical particles include chemical (e.g. co-precipitation of polymeric matrices), physicochemical (e.g. emulsion techniques) and mechanical techniques (e.g. fluidised bed coating, spray drying). Controlled coating on the inorganic core particles has been achieved with laser ablation techniques as well as with chemical vapor deposition (CVD) techniques. Recently, pharmaceutical powders were coated by physical vapor deposition (PVD) in a fluidized bed reactor. In solution, functional coatings for latexes can be, for instance, utilized in the field of biotechnology.

However, there are several difficulties with existing methods such as poor solubility in suitable solvents, particle agglomeration, long processing times and high losses that limit their applicability. The losses can be decreased with a continuous gas phase process such as spray drying, spray congealing or aerosol methods. In addition, gas phase methods enable efficient production of finely dispersed powders in well-controlled conditions with higher drug loads compared to conventional methods.

To overcome the flowability problem fine drug particles have been blended with coarse carrier particles. To improve the flowability further, the blend has been mixed with fine particle excipients, such as fine lactose, magnesium stearate, phospholipids and L-leucine function as lubricants between surfaces. Coating of the inhalable powders can also be carried in situ in particle production. For example, spray-freeze-dried proteins have been shown to result in low density particles with a rough surface. Amino acids when co-spray-dried with drugs provided surface with reduced adhesion properties. However, the coating around particles is often non-uniform and the scaling of the process is difficult in many cases. The ability to modify the surface of particles in situ in the gas phase simplifies the production dramatically and also reduces the cost of high quality particles.

Consequently a method to produce large quantities of aerosol particles containing an active agent and a surface modifying agent with well controlled surface properties so as to have superior flowability, stability, deagglomeration efficiency and/or dissolution properties would be beneficial to industry and commerce. The present invention provides a simple and efficient method which is able to produce particles with consistent and controlled properties, including particle size and size distribution, shape, crystallinity, polymorphic phase, surface roughness, composition and chemical purity. Such particles are particularly well suited for drug delivery by inhalation.

The method of this invention for the in-situ synthesis of surface modified particles can easily be used for the either nano- or micron-sized particles and for a wide variety of materials. It enables the tailoring of the surface of particles composed of a wide variety of materials. The surface modification can be varied by varying the supersaturation of the coating material during the process. The processing time is short and dry surface modified particles can be obtained directly after the particle synthesis.

2. SUMMARY OF THE INVENTION

It has been found that it is possible to produce aerosol particles having well controlled surface properties wherein the surface morphology, composition and chrystalininity can be produced continuously in an aerosol reactor. The present invention relates to a method and apparatus for the one-step production of surface modified aerosol particles containing an active agent and a surface agent in continuous or batch reactors and to particles produces by the method and apparatus. The method is particularly useful in the preparation of pharmaceutical particles suitable for, for instance, transdermal, oral or pulmonary delivery. Here an active agent can be, for instance, a therapeutic, cosmetic or diagnostic agent. A surface agent can be, for instance, an inert or active stabilizer, glidant, encapsulator, dissolution controller or morphology modifier. The surface agent can also be an active agent. Particles produced by the method exhibit improved flowability, dispersability and stability allowing, for instance, more accurate dosing and more efficient deagglomeration and thus more effective delivery to the lungs during pulmonary delivery. The particles can be further dispersed in gases, liquids or colloidal suspensions for pulmonary drug delivery, tablets, capsules, mixtures, emulsions or syrups for oral administration or injection or patches or the like for transdermal drug delivery. Furthermore, by using a variety of active and surface agents as are known in the art, the method can be applied to the production of, for instance, photochemical, catalyst, fertilizer, pigment, propellant, food, explosive, or agricultural particles. This method comprises the steps of:

- Introducing an aerosol consisting of one or more carrier gases and one or more active agent containing aerosol particles and one or more surface agents into an aerosol reactor;
- Maintaining the aerosol, for a period of time, in conditions wherein all or part of the surface agent is in the vapor phase while the active agent is largely in the liquid and/or solid phase;
- Altering the conditions of the aerosol such that all or part of the surface agent is fully or partially deposited on the surface of the active agent containing aerosol particles.

The therapeutic agent can be, for example, a systemic or local drug, a peptide or DNA based drug, an anti-inflammatory agent, a bronchodilating agent, an antiviral agent, an antibiotic agent, an immunostimulatory agent, an immunosupressive agent, an anesthetic agent, an anticancer agent, a vitamin, a hormone, an antiepileptic agent, an antifungal agent, an antioxidant, an antidiabetic agent, a muscle relaxant, and anti-HIV agent, a stimulant, a cough suppressant, a pain controller, a smoking cessation agent or an alcohol abuse agent.

3. BRIEF DESCRIPTION OF DRAWINGS

FIG. 1 shows a schematic diagram of the method of the invention

FIG. 2 shows an embodiment of the invention for producing surface modified particles from a single source of aerosol particles containing both active and surface agents FIG. 3 shows an embodiment of the invention for producing surface modified particles from two sources of aerosol particles containing active and surface agents separately FIG. 4 shows an embodiment of the invention for producing surface modified particles from a source of aerosol particles containing active agents and a gaseous source of surface agent FIG. 5 shows ELPI size distributions of the produced Salbutamol sulfate particles wherein the surface of the particle is modified with L-leucine. The surface modification is accomplished via the evaporation and heterogeneous nucleation of L-leucine vapor on the particle surface and via the evaporation and heterogeneous nucleation of L-leucine vapor and via the deposition of homogeneously nucleated L-leucine particles.

4. DETAILED DESCRIPTION OF THE INVENTION

Figure 1:
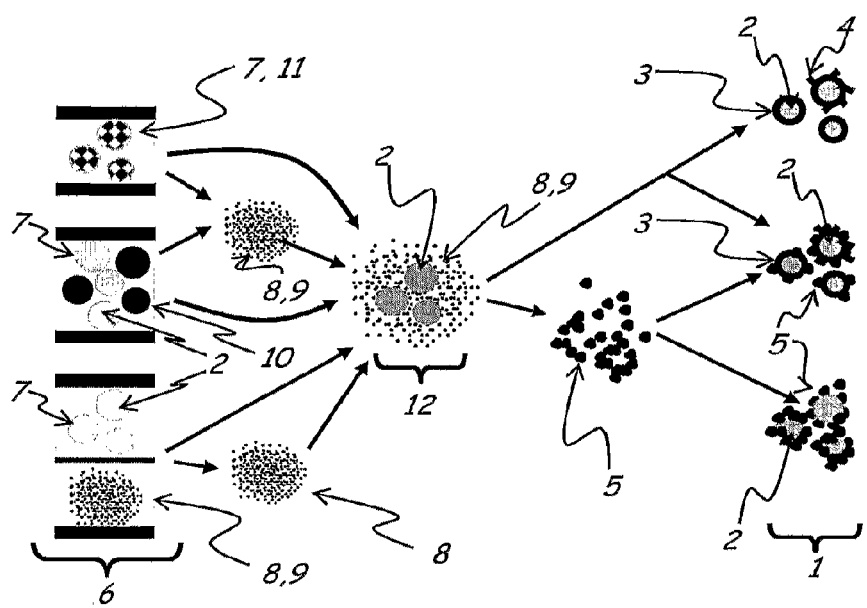

FIG. 1 shows a schematic diagram of the method of the invention for producing surface modified multicomponent aerosol particles suitable for, for instance, therapeutic, cosmetic or diagnostic use (1) containing one or more active agents (2) and one or more surface agents fully or partially covering the particle as an amorphous or crystalline coating (3), a rough, flaked or leafy structure (4), as a particle deposit of largely surface agent containing particles (5) or any combination thereof. In the method, an aerosol (6) consisting of one or more carrier gases and one or more aerosolized active agent containing aerosol particles (7) are introduced into an aerosol reactor together with one or more surface agents. An important aspect of the invention is that the active agent remains largely as a solid and/or liquid aerosol particle for the entire residence time in the reactor while the surface agent is largely in the gaseous phase for a period of time in the reactor and is subsequently reacted, or homogeneously or heterogeneously nucleated so as to deposit on the surface of the active agent containing aerosol particles. According to the invention, the surface agent can be introduced directly as a gas (8) or as gaseous precursor (9), in aerosol particles distinct from the active agent aerosol particles (10) which are subsequently fully or partially vaporized to generate a gas (8) or gaseous precursor (9) or caused to react or decompose so as to enter the gas phase, or can be introduced in the same aerosol particles as the active agent (11) which are subsequently partially vaporized or caused to react or decompose so that the surface agent fully or partially enters the gas phase. Vaporization can be accomplished by reducing the surface agent's saturation ratio by, for instance, heating, reduced pressure and/or reduced concentration in the gas phase. Consequently, an aerosol is produced containing one or more surface agents or surface agent precursors in gaseous form and one or more active agents in liquid or solid aerosol particle form (12). Various means known in the art can be used to form and/or introduce the aerosol particles such as jet or spinning disk atomizers, nebulizers, spray nozzles, air assisted or air blast nebulizers, pressurized liquid atomizers, ultrasonic nebulizers, electrosprays, vibrating orifices, or rotating aerosol generators. Other methods are possible as are known in the art. Subsequently, the aerosol conditions are then altered such that all or part of the surface agent is fully or partially incorporated on the surface of the active agent containing particle. This can be accomplished by, for instance, increasing the saturation ratio of surface agent in the reactor through, for instance, cooling, adiabatic expansion or elevating the pressure, or by chemically reaction or by, for instance, thermal or ultraviolet decomposition of surface agent precursor gas in the vapor phase or at the particle surface. By altering the rate of change of pressure, temperature and/or concentration of surface agent and/or surface agent precursor gas and/or active agent containing aerosol particles, the surface agent and/or surface agent precursor gas can be made to preferably heterogeneous nucleate or to react on the particle surface or to homogeneously nucleate to form largely surface agent containing particles (5) which are subsequently deposited on the active agent containing particle surface by interparticle collision. Additionally and preferably, by maintaining reactor conditions in a range of concentrations, pressures and/or temperatures such that the saturation ratio is maintained, for a period of time, below the amorphous vaporization saturation ratio where the surface agent molecules vaporize when not in a crystal lattice and above the crystalline vaporization saturation ratio where the surface agent molecules redeposite in a crystal lattice so as to create a crystalline film, shell, layer or flaked or leafy structure around the active agent.

Figure 2:
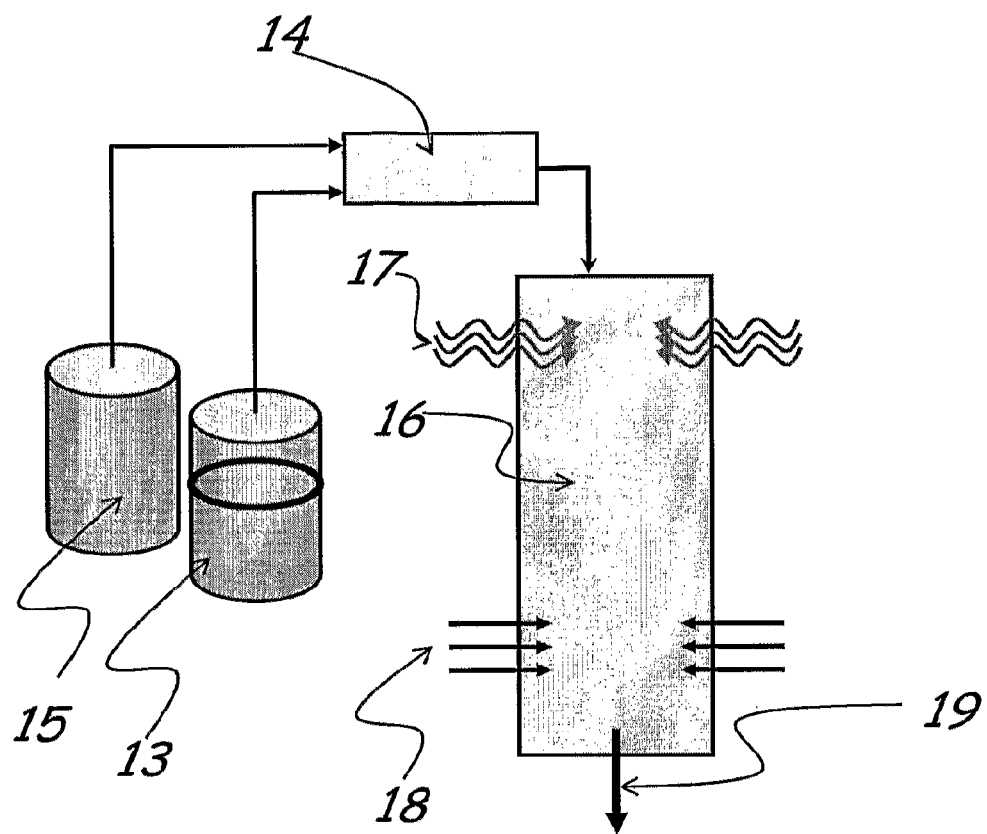

FIG. 2 shows a schematic of a preferred embodiment of the invention wherein a solution (13) containing one or more active agents and surface agents is introduced into an aerosolizer (14) together with a carrier gas (15) to produce an aerosol such that the active agent containing aerosol particles also contain essentially the same proportion of active agent(s) and surface agent(s) as in the original solution. The solution (13) may contain other components such as solvents, additives or bulking agents to allow better aerosolization or to control, for instance, the size, density, composition, stability, crystallinity, and/or morphology of the final product, though this is not necessary according to the invention. The aerosol is then introduced into the reactor (16) where energy (17) is added to raise the temperature such that the surface agent vaporizes. In one preferred embodiment, the saturation conditions are maintained such that the amorphous vaporization temperature where the surface agent molecules vaporize when not in a crystal lattice and below the crystalline vaporization temperature where the surface agent molecules redeposit in a crystal lattice so as to create a crystalline film, shell, layer or structure around the active agent. Alternately, the aerosol is quickly quenched with, for instance, a cooling gas (18) so as to increase the saturation ratio and cause, alternately, homogeneous and/or heterogeneous nucleation of the surface agent vapor in the gas phase (to form surface agent particles which then deposit on the active agent particles) or on the surface of the active agent containing particle. The nucleation route can be determined by the rate of change in the saturation conditions and by the concentration of active agent containing aerosol particles. The produced surface modified multicomponent aerosol particles (19) then can be collected by any means known in the art such as filtration, diffusion, inertial impaction, thermophoretic sampling, electrostatic precipitation or the like or directly incorporated into a powder, film, tablet or dispersion in a liquid or solid.

Figure 3:
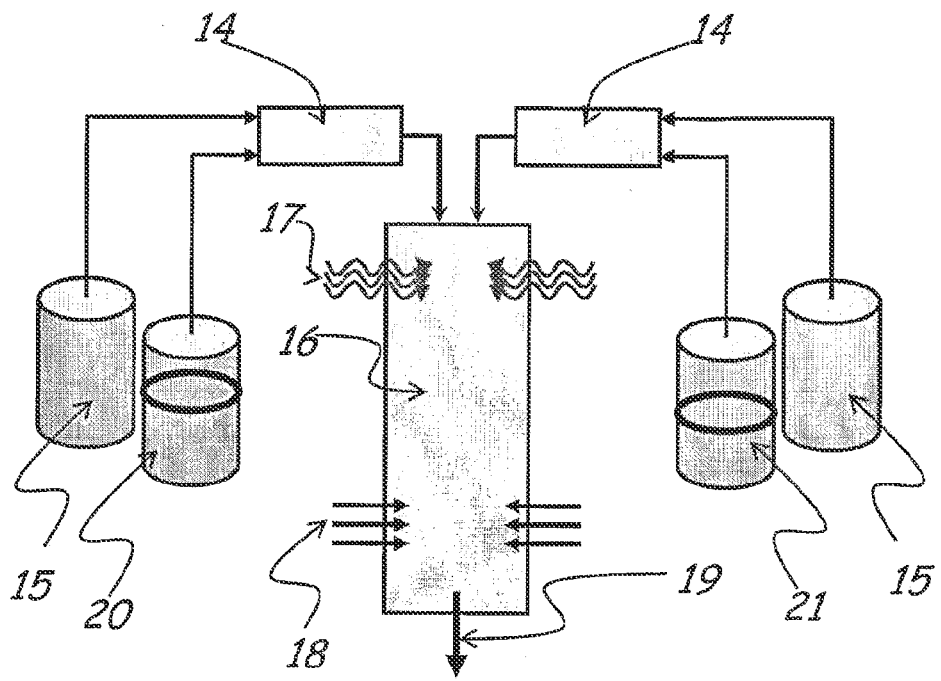

In an alternate embodiment of the invention (as is shown in FIG. 3), the surface agent and the active agent are introduced as separate aerosol flows wherein a solution (20) containing one or more active agents is introduced into an aerosolizer (14) together with a carrier gas (15) to produce an active agent containing aerosol and a solution (21) containing one or more surface agents is introduced into an aerosolizer (14) together with a carrier gas (15) to produce an surface agent containing aerosol. The solutions (20, 21) may contain other components such as solvents, additives or bulking agents to allow better aerosolization or to control, for instance, the size, density, composition, stability, crystallinity, and/or morphology of the final product, though this is not necessary according to the invention. The aerosols are then introduced into the reactor (16) where energy (17) is added to raise the temperature such that the surface agent aerosol particles fully or partially vaporize. As in the previous embodiment, the temperature of the resulting aerosol then lowered so as to homogeneous and/or heterogeneous nucleate the surface agent and thereby deposit it on the active agent particles to produce surface modified multicomponent aerosol particles (19).

Figure 4:
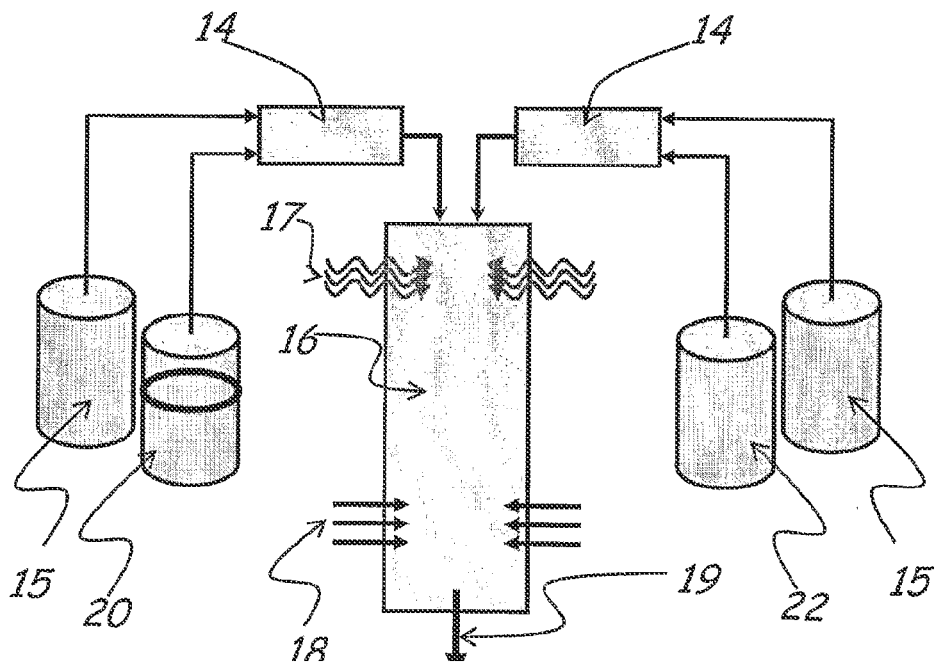

In an alternate embodiment of the invention (as is shown in FIG. 4), the active agent is introduced as an aerosol and the surface agent is introduced as a gas wherein a solution (20) containing one or more active agents is introduced into an aerosolizer (14) together with a carrier gas (15) to produce an active agent containing aerosol together with the gaseous surface agent (22) and an optional carrier gas (15). The solution (20) may contain other components such as solvents, additives or bulking agents to allow better aerosolization or to control, for instance, the size, density, composition, stability, crystallinity, and/or morphology of the final product, though this is not necessary according to the invention. The surface and active agents are then introduced into the reactor (16) where the saturation ratio of the surface agent is increased so as to result in homogeneous and/or heterogeneous nucleation of the surface agent and thereby cause it to deposit on the active agent particles to produce surface modified multicomponent aerosol particles (19).

Various energy sources can be used, when desired, to heat the aerosol reactor according to the invention. Examples include, but are not limited to, resistive, conductive, convective, radiative or nuclear or chemical heating.

It is often desirable to collect the product aerosol particles in powder form. Various methods know in the art can be used such as cyclones, electrostatic precipitators, settling chambers and filters. Other methods known in the art can be used.

In the following examples, a biocompatible peptide (L-Leucine) is used as the surface agent. Other organic and/or inorganic materials are possible according to the invention in-so-far as they or their precursors are volatalizable. Such materials include amino acids, waxes, lipids, surfactants, polymerizable momomers, initiators, catalysts, metals, oxides and the like. Amino acids can be, for instance, nonpolar, polar, aeromatic, positively or negatively charged. Waxes and lipids include lipidic materials include long-chain fatty acids, long-chain fatty alcohols, long-chain fatty esters, long-chain fatty amines, long-chain fatty amides, bile salts, surfactants and combinations thereof. Polymers include water-soluble and insoluble resins and enteric resins. Other compounds are available according to those skilled in the art and the preceding list is not intended to limit the scope of the invention in any way.

5. EXAMPLES

In order to facilitate a more complete understanding of the invention, examples are provided below. These examples are for purposes of illustration only and are not intended to limit the scope of the invention in any way. Those knowledgeable in the art can make modifications to the process, components and/or materials as appropriate. Analysis of the properties of the particles produced were carried out using Scanning Electron Microscopy (SEM), Differential Mobility Analysis (DMA), Electrical Low Pressure Impaction (ELPI) and dispersion testing according to the methods described in [Kurkela et. al "Studies on powder deagglomeration into turbulent jet flow, Advanced Gas Cleaning Technology, Eds. Kanaoka, D., Makino, H. Kamiya H., Jugei Shobo, Tokyo, 249-255, 2005].

Production of Micron Particles from an Aerosol Containing Multicomponent Aerosol Particles:

In examples 1-5, the following procedure was used to generate precursor aerosol particles according to the method described in FIG. 2. Droplets were generated using an ultrasonic nebulizer (RBI Pyrosol 7901) with a constant power level. The droplets, with a volume consumption of 0.28 to 0.44 ml/min, were carried at room temperature into a heated tube using dry nitrogen with a flow rate of 1.4 to 3.0 l/min. The tube was stainless steel with the inner diameter and length of 30 and 800 mm, respectively. At 200° C., expansion of the gas caused the rate of aerosol flow in the heated section to increase to 2.3 l/min, thus, diluted the L-leucine vapor. The actual concentration of L-leucine vapor varied from $1.6 \times 10^{-5}$ to $3.9 \times 10^{-3}$ g/l corresponding to precursor solution concentrations ranging from 0.25 to 15 g/l. The aerosol flow was laminar with a Reynolds number of 74 and the residence time approximately 9 seconds. Downsteam in the reactor, the dry microparticles and leucine vapor were simultaneously diluted by dry nitrogen gas with a flow rate of 76 l/min (Reynolds number>3000) and the leucine nucleated in the cooling section. The temperature of the cooling section varied from 23 to 74° C. The cooling gas was evenly distributed with the aid of a porous stainless steel tube having the inner diameter and length of 30 and 200 mm, respectively. The purpose of the dilution was to prevent the recondensation of the water vapor as well as losses due to diffusion and thermophoresis of particles on the cold reactor walls. The particle samples were collected by an electrostatic precipitator (In-Tox Products) onto either a plain or carbon-coated copper grid (Agar Scientific Ltd.) for characterization in SEM. Microparticles produced in Examples 1-5 were stored over silica (~0% Relative Humidity) and at 43% Relative Humidity. Over 9 months the morphology of pure salbutamol particles changed in both conditions. The morphology of the produced surface modified particles did not change.

Example 1

Production of Micronsized Salbutamol Sulphate Particles with Surface Modification by Heterogeneous Nucleation Materials: Salbutamol sulphate, L-leucine, and water.
Concentrations in water: Salbutamol 30 g/l and L-leucine 7.5 g/l.
Droplet generator: Ultrasonic nebulizer.
Operating reactor temperatures: 160° C.
Operating flow rate in reactor: Dry nitrogen 3.0 l/min.
Residence time in reactor: 7.8 s.
Dilution ratio: 26.

Figure 5:
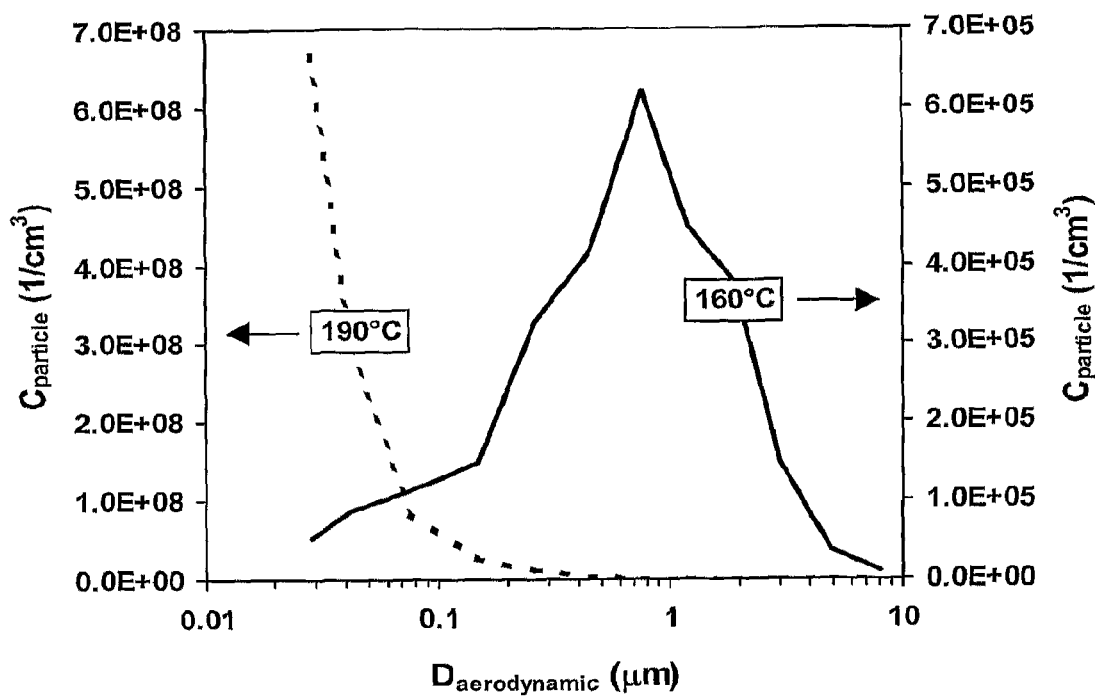
Figure 6:
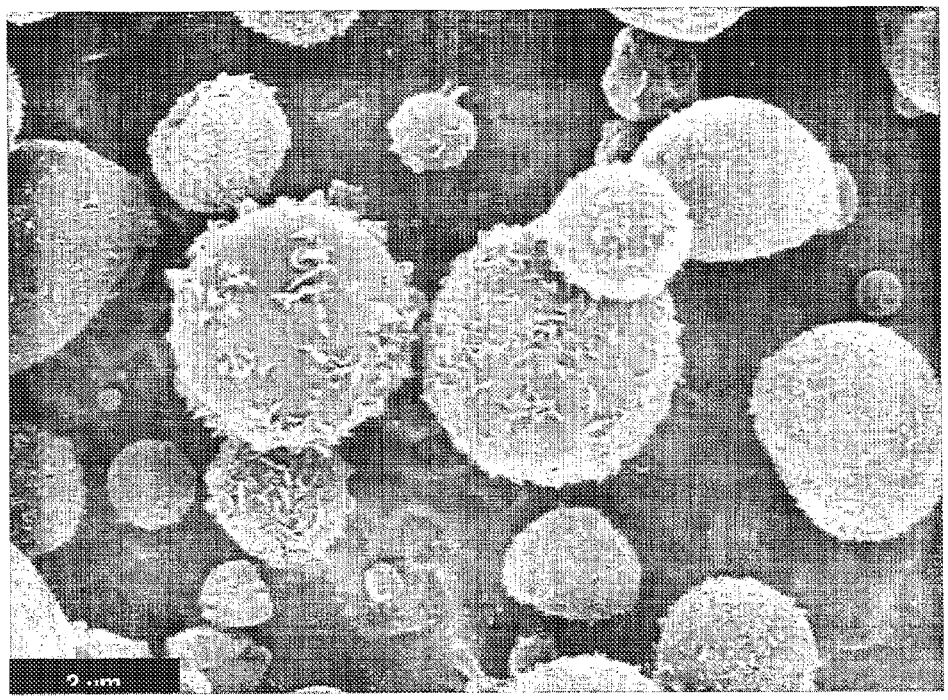
FIG. 6 shows an SEM image of Salbutamol sulfate particles surface modified with heterogeneously nucleated L-leucine flakes.

FIG. 5 (ELPI) shows the size distributions of the produced particles wherein the surface of the particle is modified with crystalline flakes of L-leucine. The surface modification is accomplished via the evaporation and heterogeneous nucleation of L-leucine vapor on the particle surface. The Geometric Number Mean Diameter (GNMD) was 0.5 μm and Geometric Standard Deviation (GSD) of the particle size distribution was 3.0. FIG. 6 shows the SEM image of the particles surface modified with heterogeneously nucleated L-leucine flakes.

Dispersion testing was conducted with lactose carrier particles at 60 l/min to examine the dispersion properties of the produced powder. The fine particle fraction (FPF, $D_a \leq 5.5$ μm) of the dispersed particles was 0.41. The mass medium aerodynamic diameter (MMAD) was 4.3 μm, GNMD 1.7 μm with a GSD 1.5.

Dispersion testing was also conducted without lactose carrier particles at 60 l/min. The fine particle fraction of the dispersed particles was 0.40. MMAD was 3.5 μM, GNMD 1.0 μm, and GSD 1.6.

Example 2

Production of Micronsized Salbutamol Sulphate Particles with Surface Modification by Homogeneous and Heterogeneous Nucleation Materials: Salbutamol sulphate, L-leucine, and water.
Concentrations in water: Salbutamol 30 g/l and L-leucine 7.5 g/l.

Droplet generator: Ultrasonic nebulizer.
Operating reactor temperatures: 190° C.
Operating flow rate in reactor: Dry nitrogen 3.0 l/min.
Residence time in reactor: 7.3 s.
Dilution ratio: 26.

Figure 7:
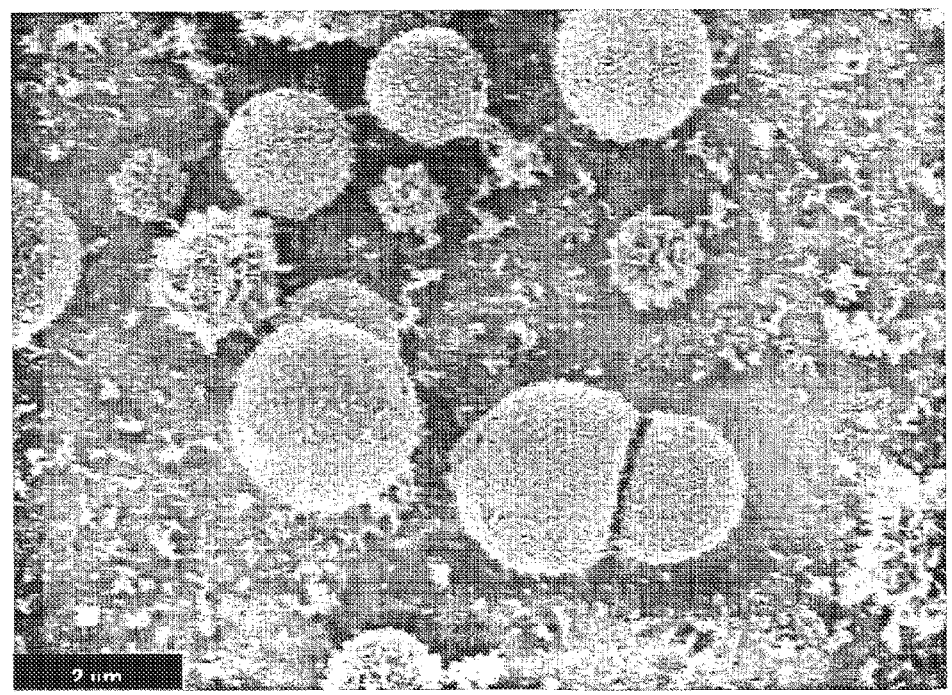
FIG. 7 shows an SEM image of Salbutamol sulfate particles surface-modified with heterogeneously nucleated L-leucine flakes as well as homogeneously nucleated L-leucine particles deposited on the surface of the particles.

FIG. 5 (ELPI) shows the size distributions of the produced particles wherein the surface of the particle is modified with crystalline flakes of L-leucine. The surface modification is accomplished via the evaporation and heterogeneous nucleation of L-leucine vapor and via the deposition of homogeneously nucleated L-leucine particles. The size distribution of the gas phase sample was bimodal. FIG. 7 shows the SEM image of the particles surface-modified with heterogeneously nucleated L-leucine flakes as well as homogeneously nucleated L-leucine particles deposited on the surface of the particles.

Dispersion testing was conducted with lactose carrier particles at 60 l/min. The fine particle fraction (FPF, $D_a \leq 5.5$ μm) of the dispersed particles was 0.34. The mass MMAD was 4.4 μm and the GNMD was 1.9 μm with a GSD of 1.6.

Dispersion testing was conducted without lactose carrier particles at 60 l/min. The fine particle fraction of the dispersed particles was 0.29. The MMAD was 2.9 μm, the GNMD was 0.9 μm and the GSD was 1.5.

Example 3

Production of Micronsized Salbutamol Sulphate Particles with Surface Modification by Homogeneous and Heterogeneous Nucleation Materials: Salbutamol sulphate, L-leucine, and water.
Concentrations in water: Salbutamol 30 g/l and L-leucine 1.0 g/l.
Droplet generator: Ultrasonic nebulizer.
Operating reactor temperatures: 190° C.
Operating flow rate in reactor: Dry nitrogen 3.0 l/min.
Residence time in reactor: 7.3 s.
Dilution ratio: 26.

Figure 8:
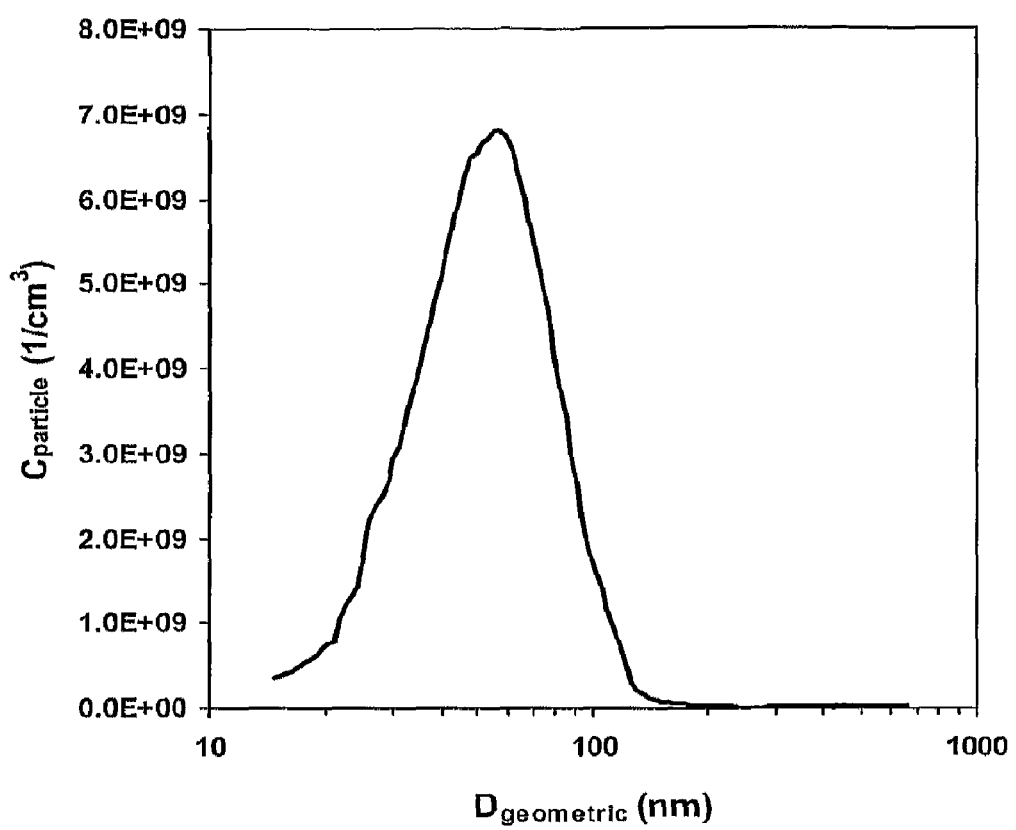
FIG. 8 shows DMA size distributions of produced Salbutamol sulfate particles wherein the surface of the particle is modified with crystalline flakes of L-leucine. The surface modification is accomplished via the evaporation and heterogeneous nucleation of L-leucine vapor and via the deposition of homogeneously nucleated L-leucine particles.
Figure 9:
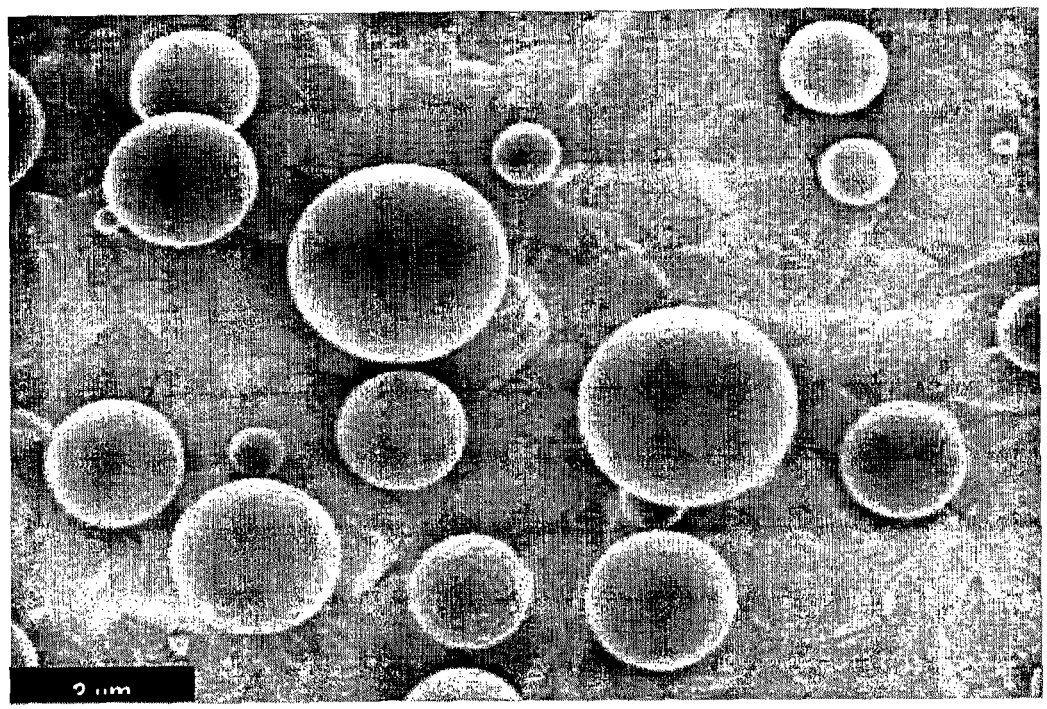
FIG. 9 shows an SEM image of Salbutamol sulfate particles surface modified with L-leucine. The surface modification is accomplished via the evaporation and heterogeneous nucleation of L-leucine vapor and via the deposition of homogeneously nucleated L-leucine particles.

FIG. 8 (DMA) shows the size distributions of the produced particles wherein the surface of the particle is modified with crystalline flakes of L-leucine. The surface modification is accomplished via the evaporation and heterogeneous nucleation of L-leucine vapor and via the deposition of homogeneously nucleated L-leucine particles. The size distribution of the gas phase sample was bimodal. FIG. 9 shows the SEM image of the particles surface modified with L-leucine.

Dispersion testing was conducted with lactose carrier particles at 60 l/min. The fine particle fraction (FPF, $D_a \leq 5.5$ μm) of the dispersed particles was 0.40. The mass medium aerodynamic diameter was MMAD was 2.9 μm and the GNMD was 0.9 μm with a GSD of 1.5.

Dispersion testing was conducted without lactose carrier particles at 60 l/min. The fine particle fraction of the dispersed particles was 0.38. The MMAD was 3.3 μm, the GNMD was 1.1 μM and the GSD was 1.7.

Example 4

Production of Micronsized Sodium Chloride Particles with Surface Modification by Heterogeneous Nucleation Materials: Sodium chloride, L-leucine, and water.
Concentrations in water: Sodium chloride 30 g/l and L-leucine 7.5 g/l.
Droplet generator: Ultrasonic nebulizer.
Operating reactor temperatures: 180° C.
Operating flow rate in reactor: Dry nitrogen 1.4 l/min.
Residence time in reactor: 15.7 s.
Dilution ratio: 55.

Figure 10:
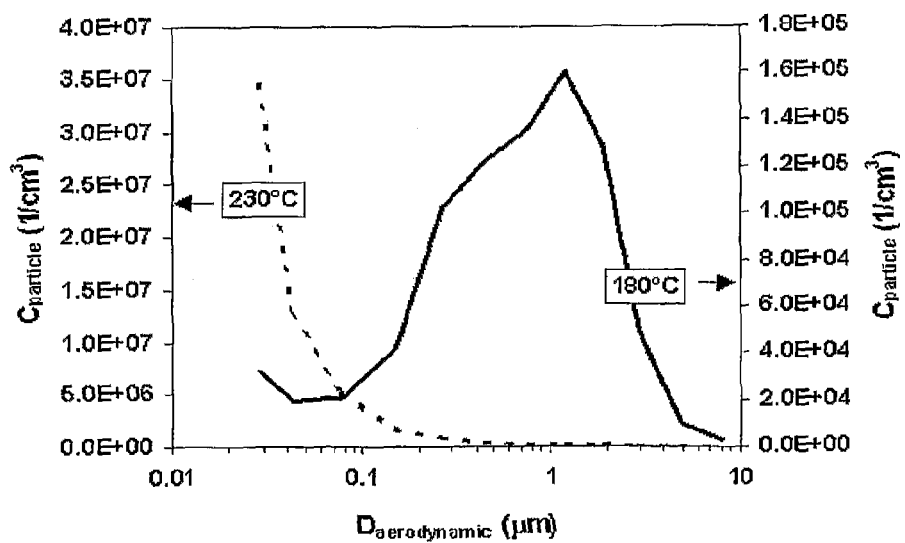
FIG. 10 shows ELPI size distributions of the produced Salbutamol sulfate particles wherein the surface of the particle is modified with crystalline flakes of L-leucine. The surface modification is accomplished via the evaporation and heterogeneous nucleation of L-leucine vapor and via the deposition of homogeneously nucleated L-leucine particles.
Figure 11:
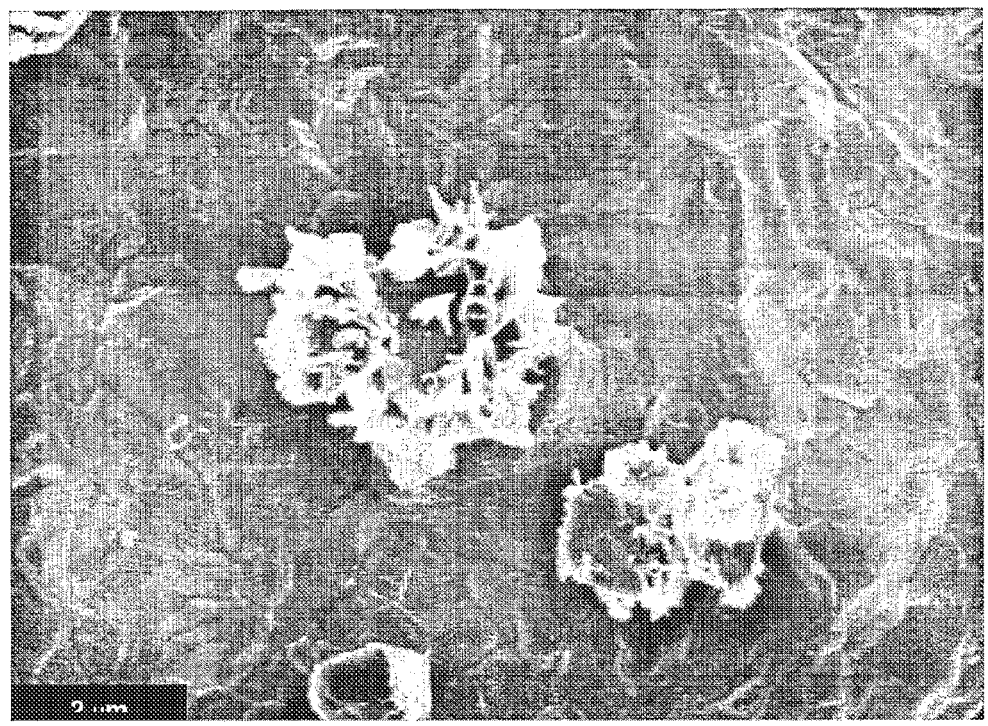
FIG. 11 shows an SEM image of NaCl particles surface modified with L-leucine flakes. The surface modification is accomplished via the evaporation and heterogeneous nucleation of L-leucine vapor and via the deposition of homogeneously nucleated L-leucine particles.

FIG. 10 (ELPI) shows the size distributions of the produced particles wherein the surface of the particle is modified with crystalline flakes of L-leucine. The surface modification is accomplished via the evaporation and heterogeneous nucleation of L-leucine vapor and via the deposition of homogeneously nucleated L-leucine particles. The GNMD was 0.6 μm and GSD 3.1. FIG. 11 shows the SEM image of the particles surface modified with L-leucine flakes.

Example 5

Production of Micronsized Sodium Chloride Particles Surface Modified by Heterogeneously and Homogeneously Nucleated L-Leucine Materials: Sodium chloride, L-leucine, and water.
Concentrations in water: Sodium chloride 30 g/l and L-leucine 7.5 g/l.
Droplet generator: Ultrasonic nebulizer.
Operating reactor temperatures: 230° C.
Operating flow rate in reactor: Dry nitrogen 1.4 l/min.
Residence time in reactor: 15.0 s.
Dilution ratio: 55.

Figure 12:
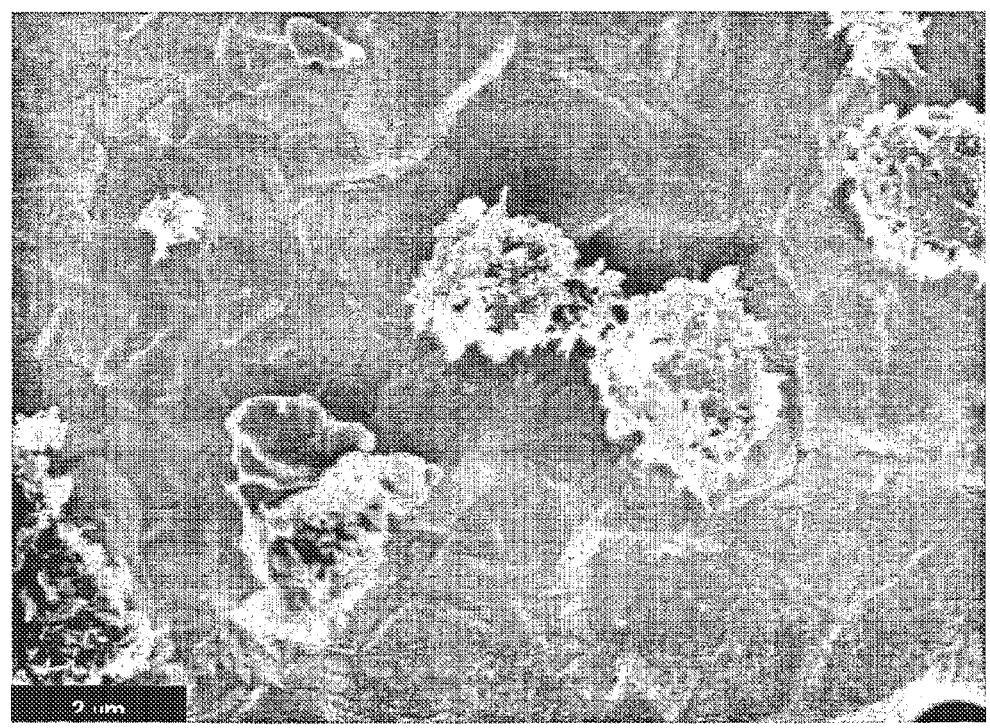
FIG. 12 shows the SEM image of NaCl particles surface-modified with L-leucine flakes. The surface modification is accomplished via the evaporation and heterogeneous nucleation of L-leucine vapor and via the deposition of homogeneously nucleated L-leucine particles.

FIG. 10 (ELPI) shows the size distributions of the produced particles wherein the surface of the particle is modified with crystalline flakes of L-leucine. The surface modification is accomplished via the evaporation and heterogeneous nucleation of L-leucine vapor and via the deposition of homogeneously nucleated L-leucine particles. The size distribution of the gas phase sample was bimodal. FIG. 12 shows the SEM image of the particles surface-modified with L-leucine flakes.

Production of Nanoparticles from an Aerosol Containing Separate Active Agent Aerosol Particles and Surface Agent Aerosol Particles:

In examples 6-12, the following general procedure was used according to the embodiment of the invention depicted in FIG. 3. Two commercially available constant output atomisers, one for the core and one for the coating material, were used to disperse the precursor solutions. The carrier gas (N$_2$) flow rate through each atomiser was adjusted to 3.3 lpm (t=25° C., P=1 atm) resulting a total flow rate of 6.6 l/min. The average feed rate of the precursor solutions to the atomisers was controlled with a needle valve to 0.4 ml/min. The produced core and coating material droplets were mixed in a narrow spiral tube with an inner diameter of 4.6 mm and length 800 mm, respectively. The flow Reynolds number in the tube was approximately 2000. After the mixing 3.1 lpm of the total aerosol flow was diverted and a flow fraction of 3.5 lpm was then carried further to a heated zone of the reactor, which consisted of a reactor tube with an inner diameter of 30 mm and length of 1200 mm placed in the furnace. The temperature in the tube was varied from 170° C. to 200° C. and the residence time was between 9.4 s and 8.8 s, respectively. A porous tube diluter was placed after the reactor. The gas temperature was 22° C. and flow rate 30 l/min. A complete mixing of aerosol and cooling gas was ensured with a mixing tube with an inner diameter of 10.2 mm and length of 500 mm. The flow Reynolds number in the mixing tube was approximately 4550 indicating turbulent flow.

Example 6

Production of Nanosized Sodium Chloride Particles Surface Modified by Heterogeneously Nucleated L-Leucine

Materials: Sodium chloride, L-leucine, and water.
Concentrations in water: Sodium chloride 4.0 g/l and L-leucine 2.2 g/l.
Droplet generator: Two Collison jet nebulizers.
Operating reactor temperatures: 170° C.
Operating flow rate in reactor: Dry nitrogen 3.5 l/min.
Residence time in reactor: 10.2 s.
Dilution ratio: 9.6.

Figure 13:
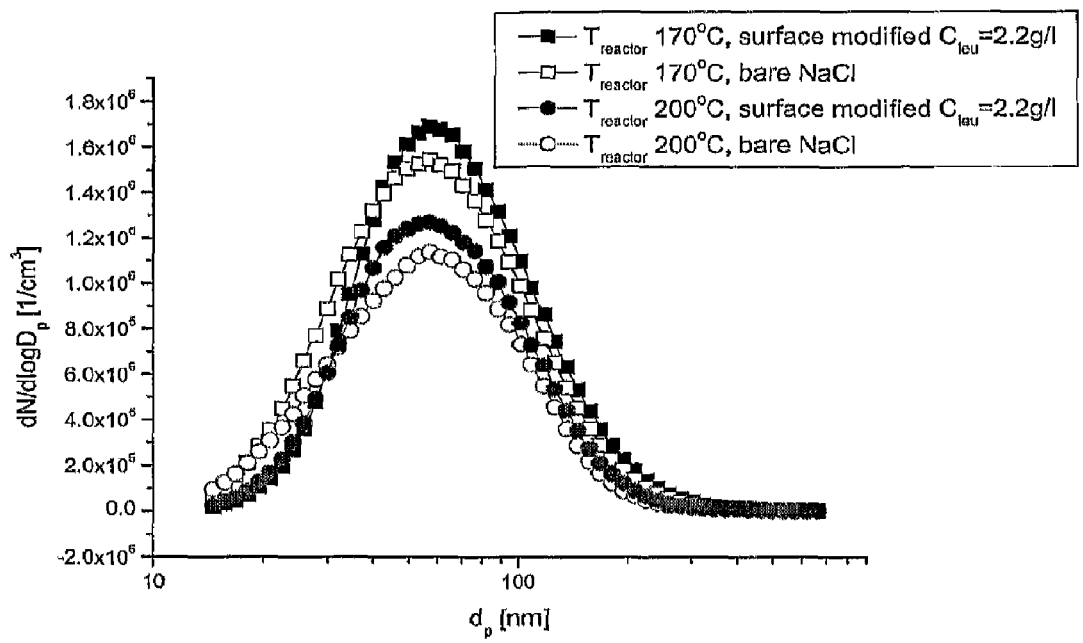
FIG. 13 shows DMA size distributions of produced NaCl particles wherein the particle is surface modified with L-leucine. The modified surface is formed via the evaporation and heterogeneous nucleation of L-leucine vapor on the particle surface.

FIG. 13 (DMA) show the size distributions of the produced particles wherein the particle is surface modified with L-leucine. The modified surface is formed via the evaporation and heterogeneous nucleation of L-leucine vapor on the particle surface. The GNMD was 65 nm and the GSD was 1.7.

Example 7

Production of Nanosized Sodium Chloride Particles with Surface Modification by Heterogeneous Nucleation of L-Leucine

Materials: Sodium chloride, L-leucine, and water.
Concentrations in water: Sodium chloride 4.0 g/l and L-leucine 2.2 g/l.
Droplet generator: Two Collison jet nebulizers.
Operating reactor temperatures: 200° C.
Operating flow rate in reactor: Dry nitrogen 3.5 l/min.
Residence time in reactor: 10.2 s.
Dilution ratio: 9.6.

Figure 14:
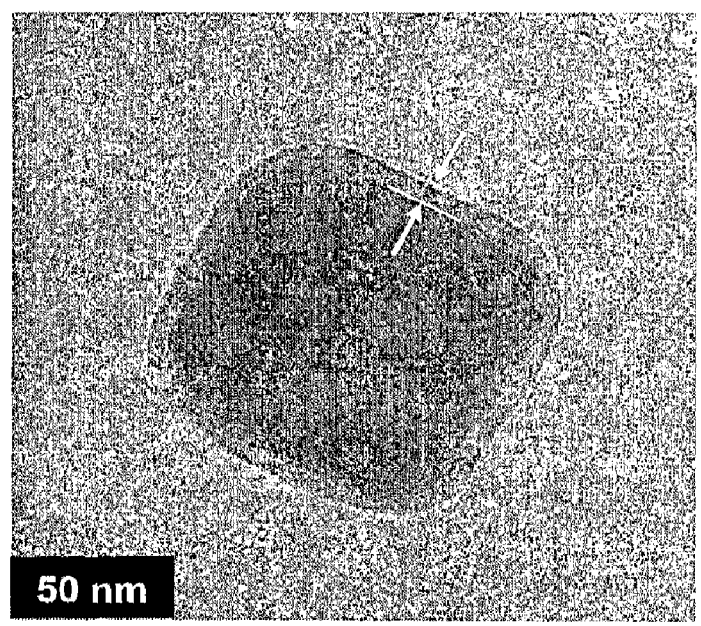
FIG. 14 shows a SEM image of NaCl particles surface-modified with L-leucine with a L-leucine concentration of 17.2 g/l. The surface modification is accomplished via the evaporation and heterogeneously nucleation of L-leucine vapor on the particle surface.
Figure 15:
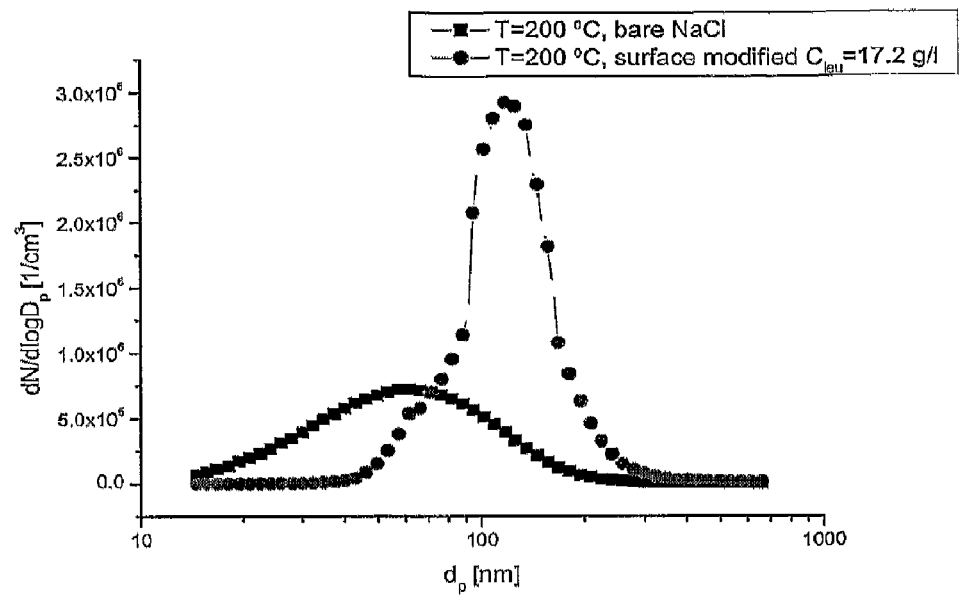
FIG. 15 shows DMA size distributions of produced NaCl particles wherein the particle is surface modified with L-leucine. The modified surface is formed via the evaporation and heterogeneous nucleation of L-leucine vapor on the particle surface.

FIG. 13 (DMA) show the size distributions of the produced particles wherein the particle is surface modified with L-leucine. The surface modification is accomplished via the evaporation and heterogeneously nucleation of L-leucine vapor on the particle surface. The GNMD 61 nm and GSD 1.7. FIG. 14 shows a SEM image of the particles surface-modified with L-leucine with a L-leucine concentration of 17.2 g/l. The surface layer is approximately 7 nm thick. FIG. 15 shows DMA measurements of the unmodified and surface modified particles.

Example 8

Production of Nanosized Lactose Particles with Surface Modification by Heterogeneous Nucleation of L-Leucine

Materials: Sodium chloride, L-leucine, and water.
Concentrations in water: Sodium chloride 4.0 g/l and L-leucine 2.2 g/l.
Droplet generator: Two Collison jet nebulizers.
Operating reactor temperatures: 170° C.
Operating flow rate in reactor: Dry nitrogen 3.5 l/min.
Residence time in reactor: 10.2 s.
Dilution ratio: 9.6.

Figure 16:
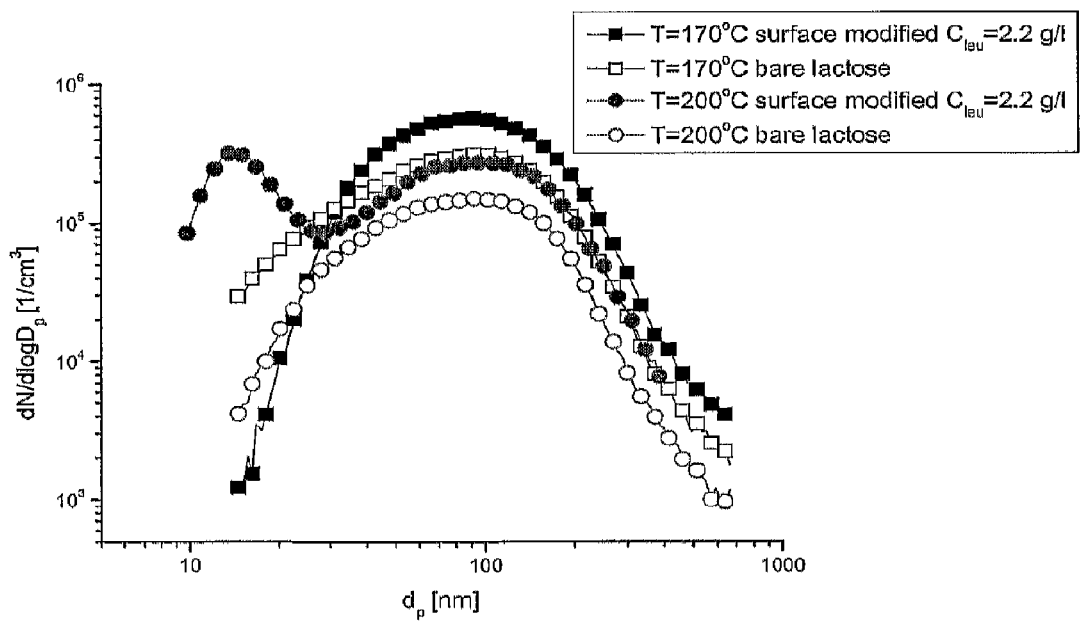
FIG. 16 shows DMA size distributions of produced Fludrocortisone particles wherein the particle is surface modified with L-leucine. The surface layer is formed via the evaporation and heterogeneous nucleation of L-leucine vapor on the particle surface.

FIG. 16 (DMA) shows the size distributions of the produced particles wherein the particle is surface modified with L-leucine. The surface is formed via the evaporation and heterogeneous nucleation of L-leucine vapor on the particle surface. The GNMD was 86 nm and the GSD was 1.7.

Example 9

Production of Nanosized Lactose Particles with Surface Modification by Heterogeneous Nucleation of L-Leucine

Materials: Sodium chloride, L-leucine, and water.
Concentrations in water: Sodium chloride 4.0 g/l and L-leucine 2.2 g/l.
Droplet generator: Two Collison jet nebulizers.
Operating reactor temperatures: 200° C.
Operating flow rate in reactor: Dry nitrogen 3.5 l/min.
Residence time in reactor: 10.2 s.
Dilution ratio: 9.6.

FIG. 16 (DMA) show the size distributions of the produced particles wherein the particle is surface modified with L-leucine. The surface is formed via the evaporation and heterogeneous nucleation of L-leucine vapor on the particle surface. The size distribution of the surface modified particles was bimodal.

Example 10

Production of Nanosized Fludrocortisone Particles with Surface Modification by Heterogeneous Nucleation of L-Leucine

Materials: Fludrocortisone 21-dipropionate, L-leucine, water, and ethanol.
Concentration in water: L-leucine 2.2 g/l.
Concentrations in ethanol: Fludrocortisone 4.0 g/l.
Droplet generator: Two Collison jet nebulizers.
Operating reactor temperatures: 170° C.
Operating flow rate in reactor: Dry nitrogen 3.5 l/min.
Residence time in reactor: 10.9 s.
Dilution ratio: 9.6.

Figure 17:
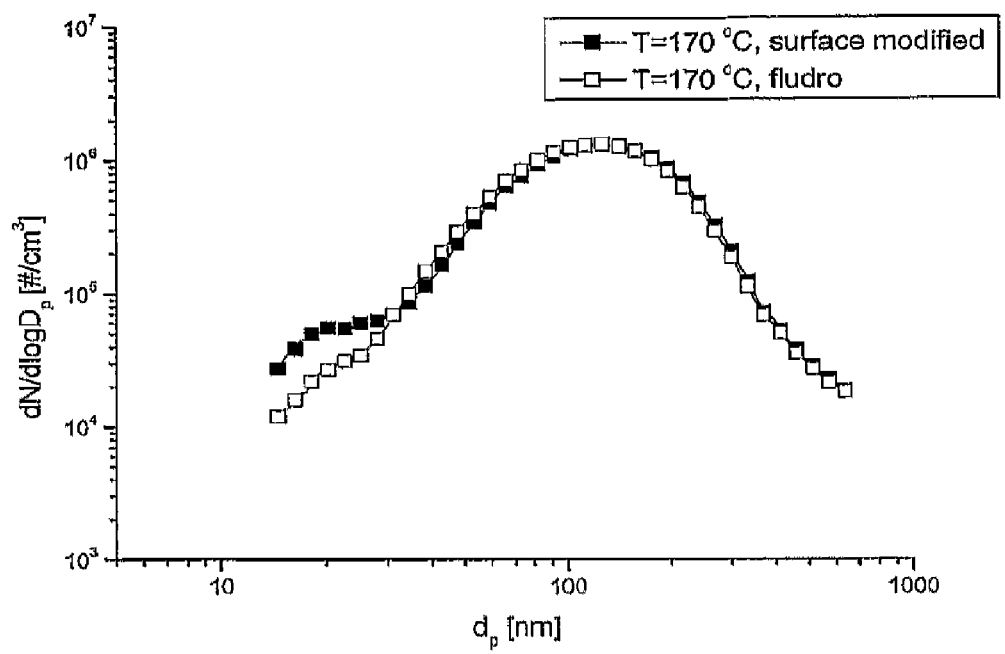
FIG. 17 shows DMA size distributions of the produced Fludrocortisone particles wherein the particle is surface modified with L-leucine. The surface layer is formed via the evaporation and heterogeneous or heterogeneous nucleation of L-leucine vapor as well as via the deposition of the homogeneously nucleated L-leucine particles on the particle surface.
Figure 18:
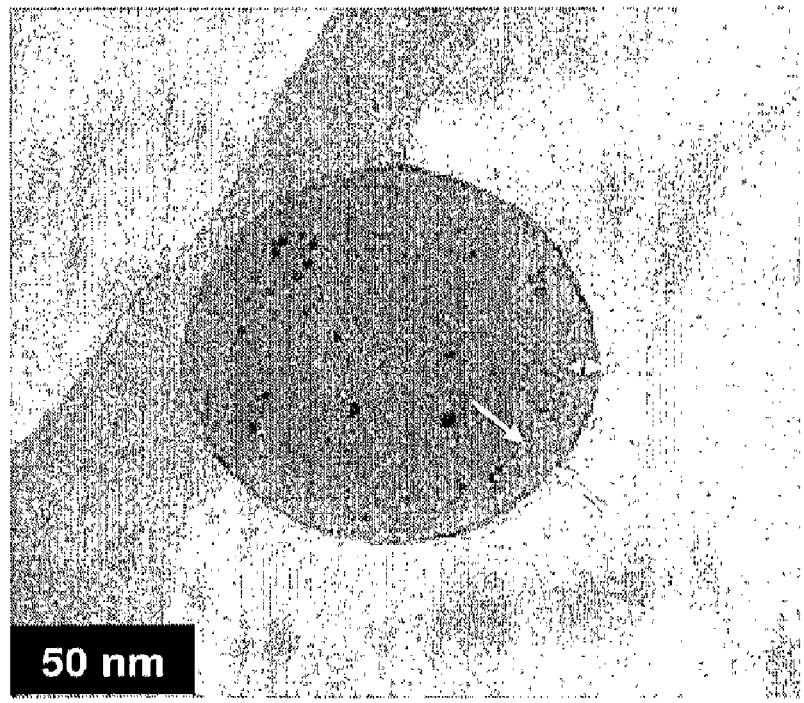
FIG. 18 shows an SEM image of Fludrocortisone particles surface-modified with L-leucine with L-leucine concentration of 17.2 g/l. The surface layer is approximately 10 nm thick.

FIG. 17 (DMA) shows the size distributions of the produced particles wherein the particle is surface modified with L-leucine. The surface is formed via the evaporation and heterogeneous nucleation of L-leucine vapor on the particle surface. The GNMD 116 nm and GSD 1.8. FIG. 18 shows the SEM image of the particles surface-modified with L-leucine coating with L-leucine concentration of 17.2 g/l. The surface layer is approximately 10 nm thick.

Example 11

Production of Nanosized Fludrocortisone Particles with Surface Modification by Homogeneous and Heterogeneous Nucleation of L-Leucine

Materials: Fludrocortisone 21-dipropionate, L-leucine, water, and ethanol.
Concentration in water: L-leucine 2.2 g/l.
Concentrations in ethanol: Fludrocortisone 4.0 g/l.
Droplet generator: Two Collison jet nebulizers.
Operating reactor temperatures: 200° C.
Operating flow rate in reactor: Dry nitrogen 3.5 l/min.
Residence time in reactor: 10.2 s.
Dilution ratio: 9.6.

FIG. 17 (DMA) shows the size distributions of the produced particles wherein the particle is surface modified with L-leucine. The coating is formed via the evaporation and heterogeneous nucleation of L-leucine vapor as well as via the deposition of the homogeneously nucleated L-leucine particles on the particle surface. The size distribution of the surface modified particles was bimodal.

Structural Stability of Surface Modified Fludro Nanoparticles

Figure 19:
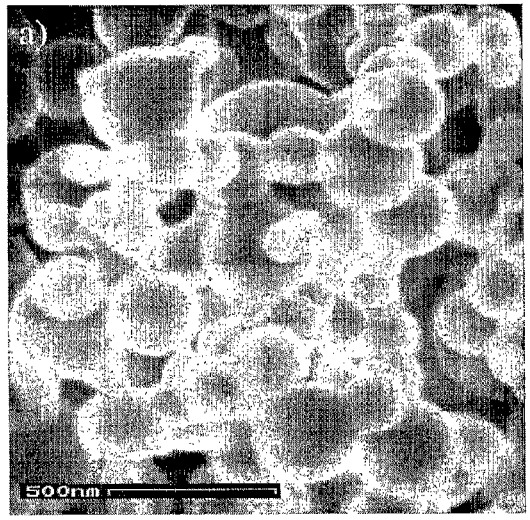
FIG. 19 shows SEM images of surface modified fludrocortisones particles after 4 and 45 weeks of storage.
Figure 19:
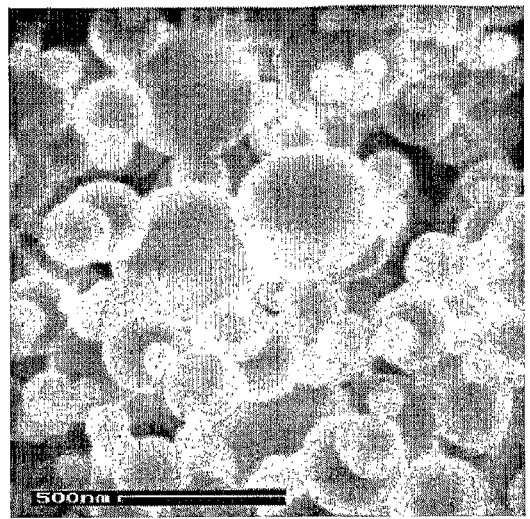
Figure 19:
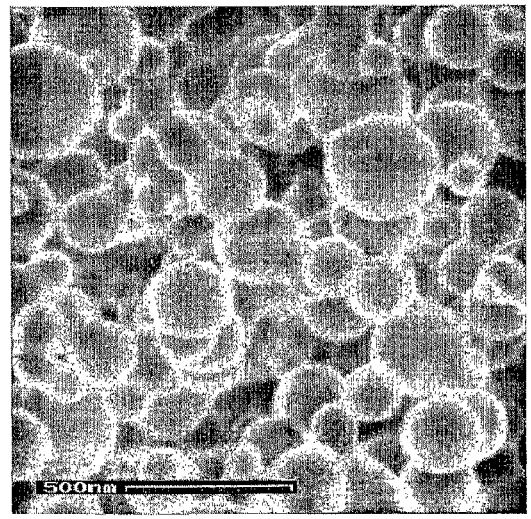
Figure 19:
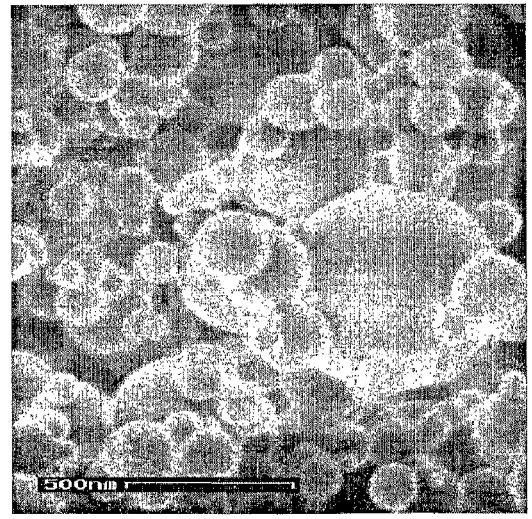

In order to study the effect of L-leucine coating on fludro nanoparticles the particles were collected on an Ag-filter and imaged with SEM. At 170° C. smooth spherical fludro particles were observed after the collection (Example 10). Without the surface of the particles began to sinter together after four weeks from the production and a chain like aggregates of the smallest particles were obtained after 45 weeks. L-leucine surface modification stabilised the particles and decreased the sintering. Spherical, smooth particles surface modified with L-leucine ($C_{leu}$=2.2-4.3 g/l) were observed even after 45 weeks as shown in FIG. 19. This indicates that there is a uniform protective layer of L-leucine around the core particles.

The pure fludro particles with smooth surface produced at 200° C. are shown in FIG. 19. A large number of ultrafine fludro particles were observed and the particles were less stable than the particles produced at 170° C. The ultrafine fludro particles were slightly sintered together immediately after the collection and no individual particles were obtained after two days of production. The particles formed large aggregates with irregular shape. No further change was then observed even after 54 weeks. The sintering of the particles was significantly reduced after surface modification with L-leucine. After 52 weeks the particles surface modified with 2.2 g/l of L-leucine were slightly sintered together. In addition, the surface structure of the particles surface had begun to change from smooth to slightly rough as shown in FIG. 19. Increasing the amount of L-leucine stabilised the particle surface structure more and decreased the sintering. After 52 weeks net like aggregates were observed while the larger particles remained separate. No change of particle surface structure was detected.

Example 12

Production of Nanosized Fludrocortisone Particles with Surface Modification by Heterogeneous Nucleation of L-Leucine Using a Rapid Mixing Chamber Materials: Fludrocortisone 21-dipropionate, L-leucine, water, and ethanol.
Concentration in water: L-leucine 7.5 g/l.
Concentrations in ethanol: Fludrocortisone 1.0 g/l.
Droplet generator: Two Collison jet nebulizers.
Operating pre-reactor flow rate: 3.5 l/min (fludro) and 3.5 l/min (L-leucine).
Operating pre-reactor temperatures: 100° C. (fludro) and 200° C. (L-leucine).
Operating reactor temperatures: 150° C. cooled to 25° C.
Operating flow rate into reactor: Dry nitrogen 7.0 l/min.
Residence time in reactor: 1 s.
Dilution ratio: 10.

Figure 20:
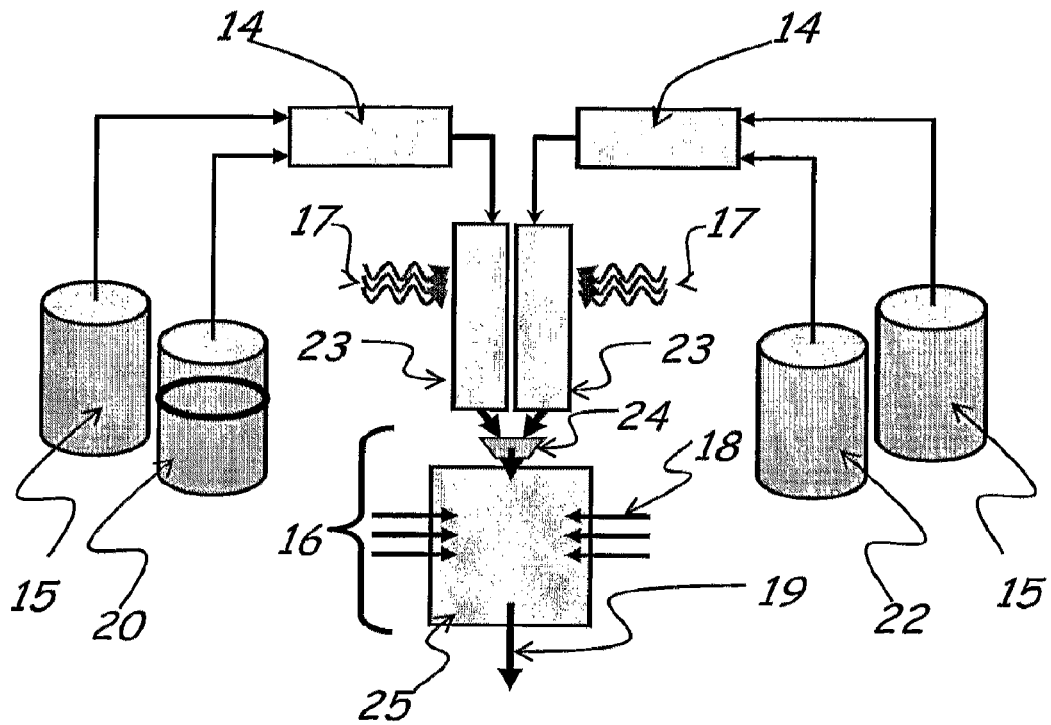
FIG. 20 shows an embodiment of the invention for producing surface modified particles from a source of aerosol particles containing active agents and a gaseous source of surface agent wherein the active agent containing aerosol is preconditioned prior to mixing with the surface agent.
Figure 21:
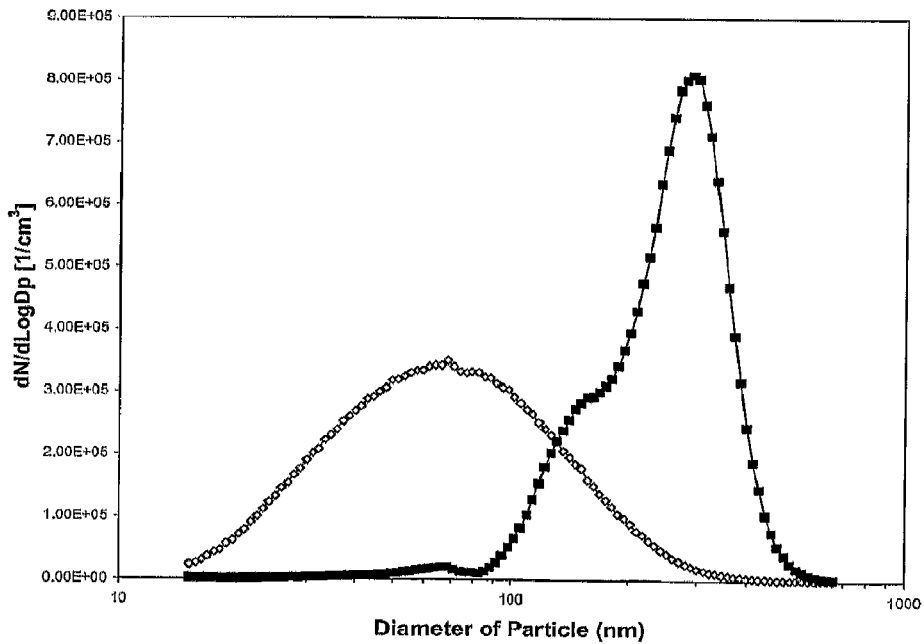
FIG. 21 shows particle size distribution for particles produced according to Example 12 with and without surface modification.
Figure 22:
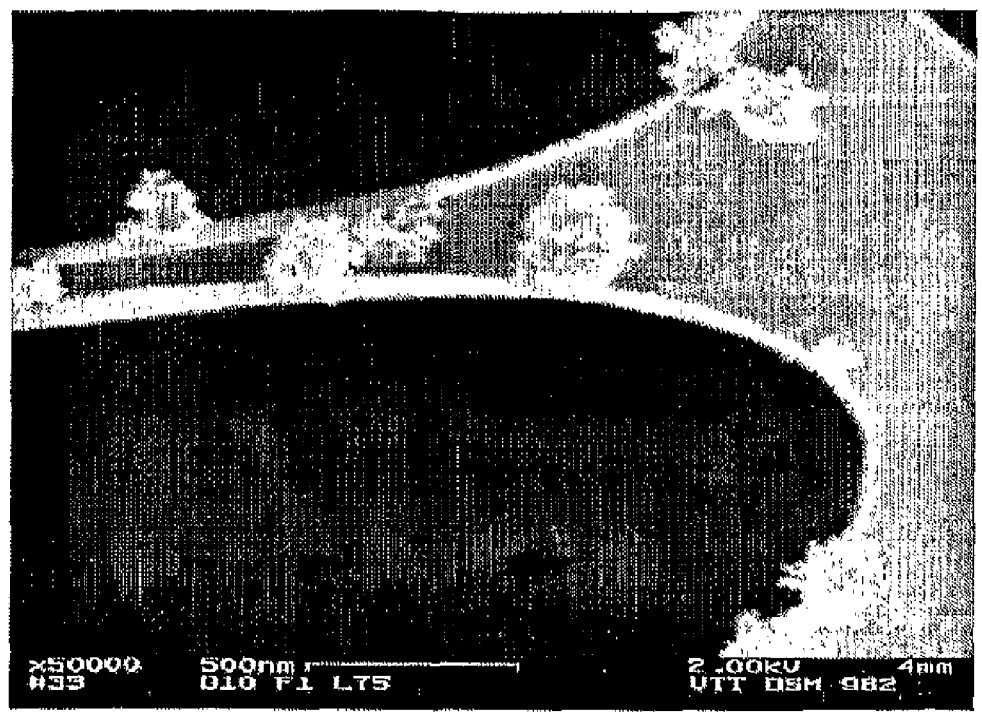
FIG. 22 show SEM images of surface modified particles produced according to Example 12.

Particles were produced in the alternate embodiment of the invention shown in FIG. 20 wherein, prior to the reactor (16) the active agent and surface agent aerosols are separately preconditioned in pre-reactors (23) wherein the leucine is vaporized and the active agent aerosol are fully or partially dried, then introduced into the reactor which consists of a mixing chamber (24) and a cooling chamber (25) wherein the conditions of the aerosol are altered by cold gas addition (18) to cool the aerosol to 25° C. FIG. 21 (DMA) shows the size distributions of the produced particles wherein the particle is surface modified with L-leucine. The surface is formed via the evaporation and heterogeneous nucleation of L-leucine vapor on the particle surface. The GNMD 120 nm and GSD 1.6. FIG. 22 shows the SEM image of the particles surface-modified with L-leucine coating with L-leucine concentration of 7.5 g/l.

Other embodiments are possible by someone knowledgeable in the state of the art according to the invention and these examples not in any way intended to limit the scope or application of the invention. Reactors can be configured in series or parallel to achieve various compositions. Additionally, reactors can be operated in full or partial batch procedures. Other energy sources can be applied to the reactor, for instance, it can be radio-frequency, microwave, acoustic, laser induction heating or some other energy source such as chemical reaction. Other systems for the production of the particles (10) for example, adiabatic expansion in a nozzle or electrospray system for the formation of particles are possible according to the invention. Other active and surface agents are also possible according to the invention and can be employed by those knowledgeable in the art.

The resulting aerosol particles can be collected as an aerosol, powder, dispersion in a liquid or solid, suspension, film, tablet, paste or solution. They can be deposited or collected in a matrix or on a surface by electrical, thermophoretic, inertial, diffusional, turbophoretic, gravitational or other forces known to the art.

What is claimed is:

1. A method for producing surface modified multicomponent aerosol particles comprising one or more active agents and one or more surface agents, the method comprising:
   introducing an aerosol of:
      one or more carrier gases,
      one or more surface agents, and
      one or more active agents in the same aerosol particle into a synthesis reactor;
   maintaining the aerosol, for a period of time, in conditions wherein all or part of the surface agent is in a vapor phase while the active agent is in a liquid and/or solid phase of unvaporized particles; and
   altering the conditions of the aerosol by increasing a saturation ratio of the one or more surface agents in the synthesis reactor, through cooling, adiabatic expansion, elevating pressure, thermal expansion or ultraviolet decomposition of a surface agent precursor gas in the vapor phase or at a particle surface,
   wherein the one or more surface agent is a biocompatible peptide, and
   the one or more active agent comprises a therapeutic agent, a diagnostic agent, or a dissolution controller.

2. The method of claim 1, wherein the one or more surface agents are fully or partially vaporized and subsequently fully or partially redeposited on a surface of unvaporized aerosol particles.

3. The method of claim 1, comprising a heterogeneous nucleation deposition route, wherein all or part of the one or more surface agent(s) fully or partially heterogeneously nucleate on a surface of unvaporized aerosol particles so as to form a film, shell, layer or structure around the active agent.

4. The method of claim 1, comprising a homogeneous nucleation deposition route, wherein the one or more surface agent(s) fully or partially homogeneously nucleates in the vapor phase to form surface agent particles, and said surface agent particles are subsequently deposited on a surface of unvaporized aerosol particles so as to fully or partially cover the unvaporized aerosol particle surface.

5. The method of claim 1, comprising a chemical vapor deposition route, wherein the one or more surface agent(s) fully or partially chemically reacts with the one or more active agent(s) and/or with unvaporized or previously deposited surface agent(s) on a surface of unvaporized aerosol particles so as to fully or partially cover the unvaporized aerosol particle surface.

6. The method of claim 1, comprising: controlling a level and rate of change of vapor saturation of the surface agent(s) by adjusting the period of time, concentration of the surface agent in the vapor phase, and/or pressure and temperature within the synthesis reactor.

7. The method of claim 1 further comprising altering the condition of the aerosol by decreasing the saturation ratio of the one or more surface agents in the synthesis reactor by heating the surface agent with heated gas, by laser, electrical, resistive, conductive, convective, radiative, acoustic and/or vibrational heating, by combustion, by chemical reaction, by adiabatic compression, or by decreasing the surface agent pressure and/or concentration by expansion or chemical reaction.

8. The method of claim 1, wherein a level of saturation of surface agent is increased by cooling the surface agent by at least one of gas addition, conductive, convective, and/or radiative cooling, adiabatic expansion, chemical reaction, by increasing the surface agent pressure by compression, or increasing the surface agent concentration by chemical reaction or decomposition of a precursor.

9. The method claim 1, wherein a saturation ratio of the active agent containing aerosol particles is maintained, for a period of time, below the surface agent's amorphous vaporization saturation ratio where the surface agent molecules vaporize when not in a crystal lattice and above the surface agent's crystalline vaporization saturation ratio where the surface agent molecules deposit in a crystal lattice, so as to create a crystalline film, shell, layer or structure around the active agent.

10. The method according to claim 1, wherein the active agent is a therapeutic, cosmetic, diagnostic, photochemical, catalyst, fertilizer, pigment, propellant, food, explosive, or agricultural agent.

11. The method according to claim 10, wherein the therapeutic agent is a systemic or local drug, a peptide or DNA based drug, an anti-inflammatory agent, a bronchodilating agent, an antiviral agent, an antibiotic agent, an immunostimulatory agent, an immunosupressive agent, an anesthetic agent, an anticancer agent, a vitamin, a hormone, an antiepileptic agent, an antifungal agent, an antioxidant, an antidiabetic agent, a muscle relaxant, and anti-HIV agent, a stimulant, a cough suppressant, a pain controller, a smoking cessation agent or an alcohol abuse agent.

12. The method of claim 1, wherein the active agent and/or surface agent containing aerosol(s) contains a solvent for the active agent and/or the surface agent.

13. The method of claim 1, wherein the one or more biocompatible peptide comprises L-leucine.

14. The method of claim 1, wherein the therapeutic agent comprises one or more of salbutamol sulfate, sodium chloride and fludrocortisone.

* * * * *